United States Patent
Gummireddy et al.

(10) Patent No.: US 11,521,753 B2
(45) Date of Patent: Dec. 6, 2022

(54) CONTEXTUAL ANNOTATION OF MEDICAL DATA

(71) Applicant: PHILIPS HEALTHCARE INFORMATICS, INC., Cambridge, MA (US)

(72) Inventors: Dileep Kumar Gummireddy, San Marcos, CA (US); Eugene Dantsker, San Diego, CA (US); Daphna Zeilingold, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 67 days.

(21) Appl. No.: 16/048,184

(22) Filed: Jul. 27, 2018

(65) Prior Publication Data
US 2020/0035366 A1  Jan. 30, 2020

(51) Int. Cl.
*G16H 80/00* (2018.01)
*G16H 10/60* (2018.01)
*G16H 40/60* (2018.01)
*A61B 5/00* (2006.01)
*G16H 15/00* (2018.01)
*G16Z 99/00* (2019.01)

(52) U.S. Cl.
CPC ............. *G16H 80/00* (2018.01); *A61B 5/681* (2013.01); *A61B 5/6898* (2013.01); *G16H 10/60* (2018.01); *G16H 40/60* (2018.01); *A61B 5/683* (2013.01); *G16H 15/00* (2018.01); *G16Z 99/00* (2019.02)

(58) Field of Classification Search
CPC ........ G16H 80/00; G16H 10/60; G16H 50/20; G16H 40/63; G16H 40/67; A61B 5/6898; A61B 5/6846; A61B 5/6861; A61B 5/6873
USPC .................................................... 705/3
See application file for complete search history.

(56) References Cited

U.S. PATENT DOCUMENTS

| | | | |
|---|---|---|---|
| 8,140,355 B2 | 3/2012 | Kashiwagi | |
| 2004/0204635 A1* | 10/2004 | Scharf | A61B 5/0002 600/323 |
| 2014/0207489 A1 | 7/2014 | Wartena et al. | |
| 2014/0358012 A1 | 12/2014 | Richards et al. | |
| 2015/0019714 A1* | 1/2015 | Shaashua | H04L 12/2818 709/224 |

(Continued)

FOREIGN PATENT DOCUMENTS

| WO | WO-2011130634 A1 * | 10/2011 | ......... G06F 19/3418 |
|---|---|---|---|
| WO | 2015183828 A1 | 12/2015 | |

OTHER PUBLICATIONS

Anonymous; Annotating medical data represented by characteristics functions; Official Gazette of the United States Patent and Trademark Office Patents (Sep. 22, 2015) (Year: 2015).*

(Continued)

*Primary Examiner* — Hiep V Nguyen

(57) ABSTRACT

A method of annotating medical data may involve receiving, by a first device, medical data from one or more sensors of one or more medical devices and non-medical event data from one or more non-medical devices. The non-medical event data may indicate a non-medical device type. The method may involve annotating the medical data according to the non-medical event data, to produce annotated medical data, and transmitting the annotated medical data to a second device.

25 Claims, 7 Drawing Sheets

(56) References Cited

U.S. PATENT DOCUMENTS

| | | | |
|---|---|---|---|
| 2016/0058333 A1* | 3/2016 | Arnold | A63B 22/0605 |
| | | | 702/19 |
| 2016/0103970 A1 | 4/2016 | Liu et al. | |
| 2016/0180222 A1 | 6/2016 | Sierhuis et al. | |
| 2017/0091412 A1 | 3/2017 | Johnson | |

OTHER PUBLICATIONS

International Search Report and Written Opinion—PCT/US2019/043635—ISA/EPO—dated Oct. 18, 2019.

* cited by examiner

FIGURE 3

| 301 | 305 | 310 | 315 | 320 | 325 |
|---|---|---|---|---|---|
| | Non-Med Device Code | Non-Med Device Manufacturer | Non-Med Device Model Number | Non-Med Event | |

| 401 | 405 | 410 | 415 | 420 | 305 | 310 | 315 | 320 | 425 |
|---|---|---|---|---|---|---|---|---|---|
| | Med Device Code | Med Device Manufacturer | Med Device Model Number | Medical Data | Non-Med Device Code | Non-Med Device Mfr | Non-Med Device Model Number | Non-Med Event | |

400

CONTEXTUAL ANNOTATION OF MEDICAL DATA

TECHNICAL FIELD

This disclosure relates to medical devices, including but not limited to medical devices that are configured for communication with other devices.

BACKGROUND

It has become commonplace for consumers to measure and track various types of health data. Some devices that are configured to measure health data also may be configured to share health data with other devices. Some such devices may be mobile devices and/or may be deployed in the home. Systems including such devices can allow remote monitoring of a user's health data. Such systems have great potential value. However, such systems also pose challenges, e.g., with regard to privacy issues, with regard to the amount and quality of health data collected, etc.

SUMMARY

The systems, methods and devices of the disclosure each have several innovative aspects, no single one of which is solely responsible for the desirable attributes disclosed herein. One innovative aspect of the subject matter described in this disclosure can be implemented in a method that involves annotating medical data. The method may involve receiving (e.g., by a control system of a first device) medical data from one or more sensors of one or more medical devices. The method may involve receiving (e.g., by the control system) non-medical event data from one or more non-medical devices. The non-medical event data may, in some instances, indicate a non-medical device type. The method may involve annotating (e.g., via the control system) the medical data according to the non-medical event data, to produce annotated medical data. The method may involve transmitting, via an interface system of the first device, the annotated medical data to a second device.

In some examples, the non-medical event data may indicate a non-medical event time and the method may involve determining (e.g., via the control system) whether to annotate the medical data according to the non-medical event data based, at least in part, on the non-medical event time. The method may involve determining (e.g., via the control system) a reliability indication for the medical data based, at least in part, on the non-medical event time. Annotating the medical data may involve providing the reliability indication.

According to some implementations, the first device may include the medical device. The method may involve sending a command and/or a query from the medical device to the non-medical device. In some implementations, the first device may be, or may include, a gateway device. The method may involve sending a command and/or a query to the medical device, to the non-medical device or to both the medical device and the non-medical device.

In some examples, the method may involve filtering (e.g., via the control system) the medical data according to the non-medical event data, to produce filtered medical data. In some such examples, the method may involve receiving (e.g., by the control system) an indication of one or more limitations on the transmission of filtered medical data and limiting (e.g., by the control system) the transmission of filtered medical data according to the indication.

According to some examples, the method may involve adjusting, by the control system, one or more sensors of a medical device, a time during which medical data is obtained, or both the one or more sensors of a medical device and the time during which medical data is obtained, based at least in part on the non-medical data.

Other innovative aspects of the subject matter described in this disclosure can be implemented in an apparatus that includes an interface system and a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

According to some examples, the control system may be configured to receive, via the interface system, medical data from one or more sensors of one or more medical devices and to receive, via the interface system, non-medical event data from one or more non-medical devices. The non-medical event data may, in some instances, indicate a non-medical device type. The control system may be configured to annotate the medical data according to the non-medical event data, to produce annotated medical data and to transmit, via the interface system, the annotated medical data to another device.

In some instances, the non-medical event data may indicate a non-medical event time. The control system may be configured to determine whether to annotate the medical data according to the non-medical event data based, at least in part, on the non-medical event time. In some such implementations, the control system may be configured to determine a reliability indication for the medical data based, at least in part, on the non-medical event time. Annotating the medical data may involve providing the reliability indication. In some examples, the annotated medical data may include non-medical device identification data and/or medical device identification data.

In some implementations, the apparatus may be, or may include, the medical device. In some such implementations, the control system may be configured to send, via the interface system, a command and/or a query from the medical device to the non-medical device.

In some instances, the apparatus may be, or may include, a gateway device. In some such examples, the control system may be configured to send, via the interface system, at least one of a command or a query to the medical device, to the non-medical device or to both the medical device and the non-medical device.

According to some examples, the control system may be configured to filter the medical data according to the non-medical event data, to produce filtered medical data. In some such examples, the control system may be configured to receive, via the interface system, an indication of one or more limitations on the transmission of filtered medical data and to limit the transmission of filtered medical data according to the indication.

In some instances, the non-medical event data may include data from a coffee machine, a stove, microwave oven or other food preparation device, an exercise machine, an environmental control device, a lighting device, a toilet, shower or other plumbing device, an entertainment device, a refrigerator, or any combination thereof. In some examples, the one or more medical devices may include a blood pressure monitor, a heart rate monitor, a glucometer, a weight scale, a pulse oximeter, an electrocardiogram device, a respiratory rate monitor, a thermometer, a drug delivery device, a bioimpedance monitor, a thermometer, a smart patch, or any combination thereof.

According to some examples, the control system may be configured to adjust one or more sensors of a medical device, to adjust a time during which medical data is obtained, or to adjust both the one or more sensors of a medical device and the time during which medical data is obtained, based at least in part on the non-medical data.

Some or all of the methods described herein may be performed by one or more devices according to instructions (e.g., software) stored on one or more non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon.

For example, the software may include instructions for controlling one or more devices to perform a method of annotating medical data. The method may involve receiving (e.g., by a control system of a first device) medical data from one or more sensors of one or more medical devices. The method may involve receiving (e.g., by the control system) non-medical event data from one or more non-medical devices. The non-medical event data may, in some instances, indicate a non-medical device type. The method may involve annotating (e.g., via the control system) the medical data according to the non-medical event data, to produce annotated medical data. The method may involve transmitting, via an interface system of the first device, the annotated medical data to a second device.

In some examples, the non-medical event data may indicate a non-medical event time and the method may involve determining (e.g., via the control system) whether to annotate the medical data according to the non-medical event data based, at least in part, on the non-medical event time. The method may involve determining (e.g., via the control system) a reliability indication for the medical data based, at least in part, on the non-medical event time. Annotating the medical data may involve providing the reliability indication.

According to some implementations, the first device may include the medical device. The method may involve sending a command and/or a query from the medical device to the non-medical device. In some implementations, the first device may be, or may include, a gateway device. The method may involve sending a command and/or a query to the medical device, to the non-medical device or to both the medical device and the non-medical device.

In some examples, the method may involve filtering (e.g., via the control system) the medical data according to the non-medical event data, to produce filtered medical data. In some such examples, the method may involve receiving (e.g., by the control system) an indication of one or more limitations on the transmission of filtered medical data and limiting (e.g., by the control system) the transmission of filtered medical data according to the indication.

According to some examples, the method may involve adjusting, by the control system, one or more sensors of a medical device, a time during which medical data is obtained, or both the one or more sensors of a medical device and the time during which medical data is obtained, based at least in part on the non-medical data.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

BRIEF DESCRIPTION OF THE DRAWINGS

FIG. 3 shows a format for non-medical event data according to one example.

FIG. 4 shows a format for annotated medical data according to one example.

DETAILED DESCRIPTION

Figure 1:
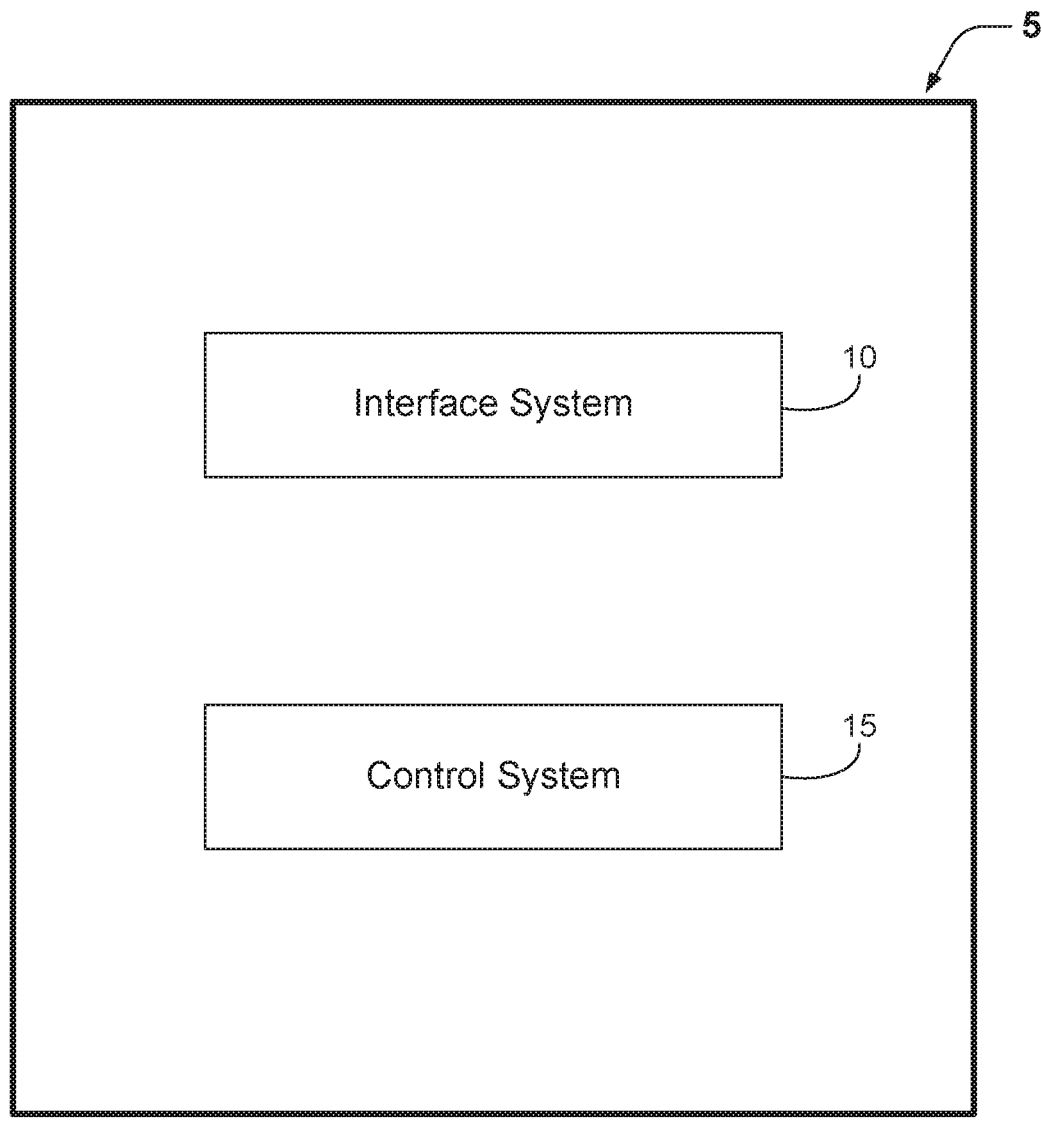
FIG. 1 is a block diagram that shows examples of components of an apparatus that may be configured to perform at least some of the methods disclosed herein.

The following description is directed to certain implementations for the purposes of describing the innovative aspects of this disclosure. However, a person having ordinary skill in the art will readily recognize that the teachings herein may be applied in a multitude of different ways. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, global navigation satellite system (GNSS) receivers/navigators, cameras, digital media players (such as MP3 players), camcorders, game consoles, wrist watches, electronic reading devices (e.g., e-readers), mobile health devices, and a variety of EMS devices. Thus, the teachings are not intended to be limited to the implementations depicted solely in the Figures, but instead have wide applicability as will be readily apparent to one having ordinary skill in the art.

As noted above, some consumers are now routinely measuring and tracking various types of health data. As used herein, "health data" may include, but is not limited to, physiological data (such as body temperature data, respiration rate data, oxygen saturation data, blood glucose data, blood pressure data, heart rate data, data indicating electrical activity of a user's heart, actigraphy data and/or blood alcohol data), exercise data, including but not limited to data from exercise machines and fitness tracker data, sleep monitor data, body mass data, food consumption data and/or beverage consumption data.

Accordingly, health data may be measured by medical devices and non-medical devices. Various examples of medical devices and non-medical devices are provided herein. As used herein, the term "medical device" encompasses all devices that fall under the definition of Section 201(h) of the Federal Food Drug & Cosmetic (FD&C) Act. Examples of such medical devices include, but are not limited to, blood pressure monitors, heart rate monitors, glucometers, weight scales, pulse oximeters, electrocardiogram devices, respiratory rate monitors, thermometers, sleep monitors, bioimpedance monitors and thermometers.

However, the term "medical device" as used herein also may refer to drug delivery devices and other devices that are excluded from being classified as medical devices under the exception of part 3 of Section 201(h), which refers to a device that is "intended to affect the structure or any function of the body of man or other animals, and which does not achieve its primary intended purposes through chemical action within or on the body of man or other animals" and "which is not dependent upon being metabolized for the achievement of its primary intended purposes." For example, a wearable device that is configured to administer a drug, a hormone or another substance would also be a "medical device" as the term is used in this disclosure. As used herein, the meaning of the term "wearable device" will encompass devices that may be worn by a user (e.g., via an arm band, a wrist band, a chest strap, etc.), devices that may be attached to a user's skin (e.g., via adhesive material) and devices that may be implanted, at least temporarily, in a user's body.

Some examples of such wearable medical devices are provided in U.S. Pat. No. 9,721,409, entitled "BIOMETRICS FOR USER IDENTIFICATION IN MOBILE HEALTH SYSTEMS," which is hereby incorporated by reference. Some wearable medical devices that are disclosed in U.S. Pat. No. 9,721,409 may be implemented as patches that may be attached to a user's skin. Some such wearable medical devices may include a sensor system that is capable of monitoring heart rate data, data indicating electrical activity of the user's heart, the user's body temperature, the user's blood glucose data, blood alcohol data, etc. Some wearable medical devices that are disclosed in U.S. Pat. No. 9,721,409 may include a substance delivery system, such as a drug and/or hormone delivery system. Some such devices may include a control system and/or may be capable of communicating with one or more other devices via wireless interfaces. Such medical devices may be referred to herein as "smart patches."

As used herein, a "non-medical device" may refer to broadly to any device that is not a medical device. However, the term "non-medical device" may be used herein to refer more specifically to a device that is capable of providing some form of health data, but which is not a medical device. Examples of such non-medical devices include, but are not limited to, coffee machines, food preparation devices such as stoves and microwave ovens, exercise machines, environmental control devices, such as thermostats, heating units and air conditioning units, lighting devices, toilets, plumbing devices, such as showers and sinks, entertainment devices, refrigerators, etc.

Some medical devices and non-medical devices may be configured to share health data with one or more other devices. For example, some medical devices and non-medical devices may be configured to function as "Internet of Things" (IoT) devices. Some such devices are configured for wired or wireless communication with other devices. For example, some IoT-enabled medical devices and non-medical devices may be configured for wired or wireless communication via Internet Protocol version 4 (IPv4) or Internet Protocol version 6 IPv6. Some such devices may be mobile devices and/or may be deployed in the home. Systems including such devices can allow remote monitoring and/or evaluation of a user's health data. Such systems have significant potential value.

However, such systems also pose challenges. Some such challenges involve privacy issues. Other challenges involve the quantity and/or quality of health data that is collected by such systems. For example, some medical data may have reduced value when evaluated without the context of when and/or how the medical data was collected, relative to other factors that can affect the patient's physiological state. Such factors may include, but are not limited to, whether the patient has recently exercised, whether the patient has recently eaten, whether the patient has recently consumed a caffeinated beverage, the temperature of the environment in which the user is located, etc.

For example, a patient's blood pressure measurements and/or other heart-related measurements may fluctuate during the day. Without contextual information, such as exercise data, caffeine consumption data, etc., these fluctuations could result in an erroneous evaluation of the patient's actual state of health.

Some implementations disclosed herein involve methods of annotating medical data. Some such methods may involve receiving, by a first device, medical data from one or more sensors of one or more medical devices and non-medical event data from one or more non-medical devices. The non-medical event data may indicate a non-medical device type. Some methods may involve annotating the medical data according to the non-medical event data, to produce annotated medical data, and transmitting the annotated medical data to a second device. Some implementations may involve determining whether to annotate the medical data according to the non-medical event data based, at least in part, on a non-medical event time. In some examples, a reliability indication may be determined for the medical data based, at least in part, on the non-medical event time. Various examples are described below.

Particular implementations of the subject matter described in this disclosure can be implemented to realize one or more of the following potential advantages. In some examples, adding contextual information to medical data may allow for more accurate analysis of the medical data. In some implementations, contextual information may indicate how reliable the medical data may be. In some examples, contextual information may be used to determine when or whether to obtain medical data.

FIG. 1 is a block diagram that shows examples of components of an apparatus that may be configured to perform at least some of the methods disclosed herein. In some examples, the apparatus 5 may be, or may include, a medical device, a non-medical device, a gateway device, a mobile device, a personal computer, a desktop computer or another device that is configured to perform at least some of the methods disclosed herein. In some examples, the apparatus 5 may be, or may include, a server. According to some examples, the apparatus 5 may be a client device that is configured for communication with a server, via a network interface. The components of the apparatus 5 may be implemented via hardware, via software stored on non-transitory media, via firmware and/or by combinations thereof. The types and numbers of components shown in FIG. 1, as well as other figures disclosed herein, are merely shown by way of example. Alternative implementations may include more, fewer and/or different components.

In this example, the apparatus 5 includes an interface system 10 and a control system 15. The interface system 10 may include one or more network interfaces, one or more wireless interfaces, one or more interfaces between the control system 15 and a sensor system, one or more interfaces between the control system 15 and a memory system and/or one or more external device interfaces (such as one or more universal serial bus (USB) interfaces). In some implementations, the interface system 10 may include a user interface system. The user interface system may be configured for receiving input from a user. In some implementations, the user interface system may be configured for providing feedback to a user. For example, the user interface system may include one or more displays with corresponding touch and/or gesture detection systems. In some examples, the user interface system may include one or more microphones and/or speakers. According to some examples, the user interface system may include apparatus for providing haptic feedback, such as a motor, a vibrator, etc. The control system 15 may, for example, include a general purpose single- or multi-chip processor, a digital signal processor (DSP), an application specific integrated circuit (ASIC), a field programmable gate array (FPGA) or other programmable logic device, discrete gate or transistor logic, and/or discrete hardware components.

In some examples, the apparatus 5 may be implemented in a single device. However, in some implementations, the apparatus 5 may be implemented in more than one device. In some such implementations, functionality of the control system 15 may be included in more than one device. In some examples, the apparatus 5 may be a component of another device.

Figure 2:
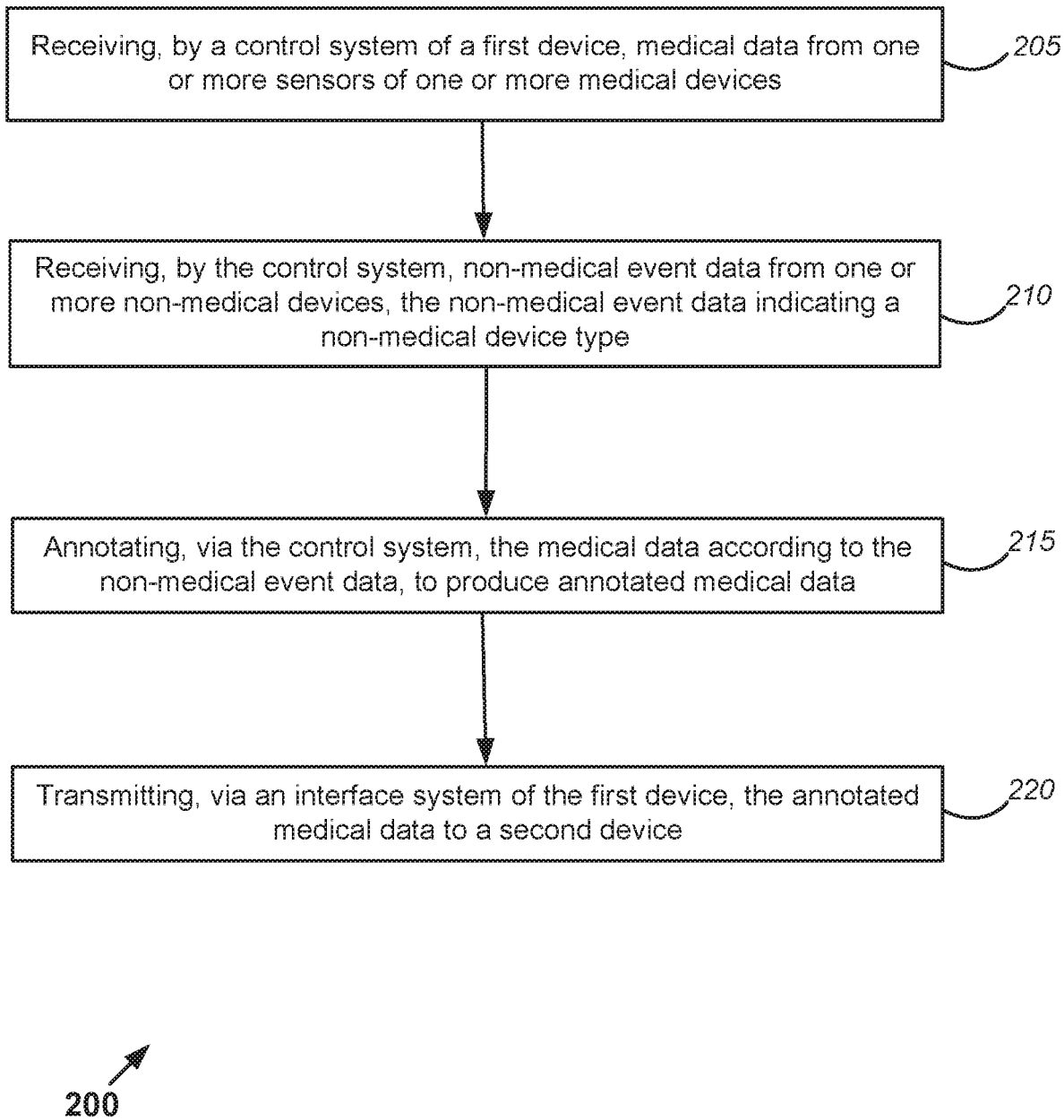
FIG. 2 is a flow diagram that shows blocks of a method of annotating medical data according to one example.

FIG. 2 is a flow diagram that shows blocks of a method of annotating medical data according to one example. The method 200 may, for example, be implemented by control system (such as the control system 15) that includes one or more processors and one or more non-transitory memory devices. As with other disclosed methods, the blocks of method 200 are not necessarily performed in the order shown in FIG. 2. Moreover, alternative methods may include more or fewer blocks.

According to this example, block 205 involves receiving, by a control system of a first device, medical data from one or more sensors of one or more medical devices. The one or more medical devices may include a blood pressure monitor, a heart rate monitor, a glucometer, a weight scale, a pulse oximeter, an electrocardiogram device, a respiratory rate monitor, a thermometer, a drug delivery device, a bioimpedance monitor, a thermometer and/or a smart patch. The first device may, in some examples, reside in a home. In some implementations, the first device may be a medical device. In some examples, block 205 may involve receiving the medical data from one or more of the medical device's sensors. Alternatively, or additionally, if the first device is a medical device, block 205 may involve receiving the medical data from one or more sensors of another medical device. In alternative implementations, the first device may be a non-medical device, such as a gateway device, a smart phone or another type of device. In some examples, block 205 may involve receiving the medical data from another device, which may or may not be a medical device. For example, block 205 may involve receiving the medical data from another device that has forwarded the medical data to the first device.

In this example, block 210 involves receiving, via the interface system, non-medical event data from one or more non-medical devices. According to some implementations, the non-medical event data includes health data. The non-medical event data may vary according to the particular implementation, e.g., according to the number of "smart" or IoT non-medical devices in a user's home, according to the capabilities of each such non-medical device and/or the type of non-medical event data that has been requested from the non-medical device. The non-medical event data may, for example, include data from a coffee machine, a stove, microwave oven or other food preparation device, an exercise machine, an environmental control device, a lighting device, a toilet, shower or other plumbing device, an entertainment device, a refrigerator, or any combination thereof. According to this example, the non-medical event data indicates a non-medical device type.

FIG. 3 shows a format for non-medical event data according to one example. Other examples of formats for the non-medical event data 300 may include more or fewer fields and/or fields in a different sequence. In this example, field 305 includes a non-medical device code that corresponds with a non-medical device type (e.g., coffee maker, refrigerator, etc.). Here, field 310 indicates the manufacturer of the non-medical device and field 315 indicates the model number, or code, of the non-medical device. According to this example, field 320 includes data regarding a non-medical event. In the example shown in FIG. 3, the non-medical event data 300 includes fields 301 and 325, which may include a header, a source address, a destination address, a checksum field, a total length field, a time-to-live field, one or more flags, etc.

The field 305 may, in some examples, indicate that the non-medical device is a coffee machine. In some such examples, the field 320 may indicate that the coffee machine has been switched on or off, that a particular amount of coffee has been dispensed from the coffee machine, that a coffee capsule has been inserted into the coffee machine, etc.

In some instances, the field 305 may indicate that the non-medical device is an exercise machine. In some such examples, the field 320 may indicate that the exercise machine has been switched on or off, a number of calories that a user has burnt by using the exercise machine, etc.

In some instances, the field 305 may indicate that the non-medical device is a smart refrigerator. In some such examples, the field 320 may indicate that the smart refrigerator has been opened or closed, a type or quantity of food that a user has removed from the smart refrigerator, etc., depending on the capabilities of the smart refrigerator.

In other examples, the field 305 may indicate that the non-medical device is a toilet. In some such examples, the field 320 may indicate a toilet-flushing event, which may indicate the mass or volume of the flush, an analysis of the contents of the toilet, etc. In still other examples, the field 305 may indicate that the non-medical device is a thermostat. In some such examples, the field 320 may indicate a room temperature and/or a thermostat temperature setting.

According to the implementation shown in FIG. 2, block 215 involves annotating, via the control system, the medical data according to the non-medical event data, to produce annotated medical data. In this example, block 220 involves transmitting, via an interface system of the first device, the annotated medical data to a second device.

FIG. 4 shows a format for annotated medical data according to one example. Other examples of formats for the annotated medical data 400 may include more or fewer fields and/or fields in a different sequence. In this example, field 405 includes a medical device code that corresponds with a medical device type (e.g., heart rate monitor, glucometer, blood pressure monitor, etc.). Here, field 410 indicates the manufacturer of the medical device and field 415 indicates the model number, or code, of the medical device. According to this example, field 420 includes medical data corresponding to a measurement via one or more sensors of the medical device.

According to this example, the process of generating the annotated medical data 400 involves receiving the non-medical event data 300, discarding fields 310 and 325 and adding fields 305-320 to a packet of annotated medical data 400. In the example shown in FIG. 4, the annotated medical data 400 includes fields 401 and 425, which may include a header, a source address, a destination address, a checksum field, a total length field, a time-to-live field, one or more flags, etc.

According to some implementations, the non-medical event data 300 may indicate a non-medical event time. In some examples, the non-medical event time may be included in the field 320 and in other examples the non-medical event time may be included in another field. According to some such examples, a control system (such as the control system 15 of FIG. 1) may be configured to determine whether to annotate the medical data according to the non-medical event data based, at least in part, on the non-medical event time.

For example, the non-medical event data may be from an aerobic exercise machine, such as a treadmill, and the medical data may include heart rate data, blood pressure data, or other heart-related data. However, the non-medical event time may indicate that the exercise took place more than a threshold time before the medical data were obtained, e.g., more than 10 or 15 minutes before the medical data were obtained. In some implementations, the control system may determine not to annotate the medical data according to the non-medical event data based on a time interval between the non-medical event time and the time at which the medical data were obtained.

In some implementations, a control system may be configured to determine a reliability indication for the medical data based, at least in part, on the non-medical event time. Annotating the medical data may involve providing the reliability indication, e.g., in the field 320, in one of the fields 425, etc.

For example, if the non-medical event data were from an aerobic exercise machine and the medical data includes heart-related data, the reliability indication may be based, at least in part, on a time interval between the non-medical event time and the time at which the medical data were obtained. If, for example, the non-medical event time indicates that the exercise took place less than a threshold time before the medical data were obtained, e.g., less than 1 minute, the reliability indication may indicate that the medical data are not reliable. If the non-medical event time indicates that the exercise took place more than 1 minute but less than 5 minutes before the medical data were obtained, the reliability indication may indicate that the medical data are potentially unreliable. If the non-medical event time indicates that the exercise took place more than a threshold time before the medical data were obtained, e.g., more than 10 or 15 minutes before the medical data were obtained, the reliability indication may indicate that the medical data are likely to be reliable.

In some implementations, the non-medical event data 300, the annotated medical data 400, or both, may indicate a code, a number, etc., corresponding with a person. The person may, for example, be a registered owner of a medical device or a non-medical device. According to some examples, the person may be identified according to one or more user identification methods, which may be optically-based, ultrasonically-based, radio frequency (RF)-based, etc. Some such examples may involve obtaining biometric data from a user and determining whether the biometric data matches previously-acquired biometric data. In some implementations the biometric data may include fingerprint data, facial image data, subdermal data and/or other types of biometric data. Such implementations may be useful for a context in which more than one person may be using a medical device or a non-medical device.

Figure 5:
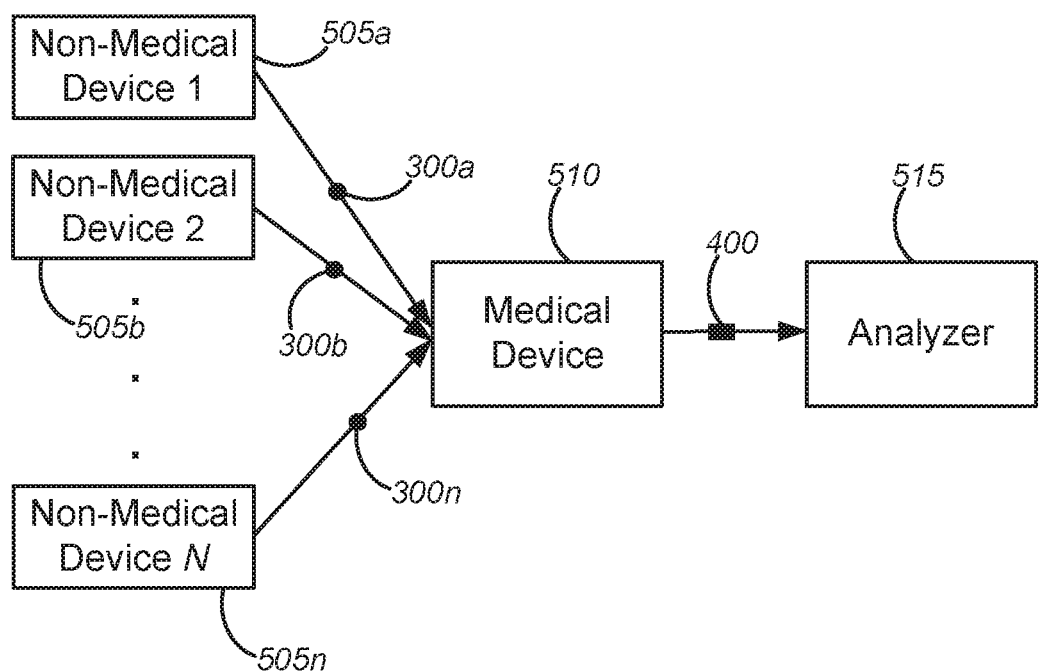
FIG. 5 shows an example of a system in which a medical device is configured to annotate medical data.

FIG. 5 shows an example of a system in which a medical device is configured to annotate medical data. The medical device 510 may include a control system and an interface system, such as the interface system 10 and the control system 15 that are shown in FIG. 1. The medical device 510 also may include a sensor system that includes one or more sensors that are configured for obtaining the medical data.

In this example, non-medical devices 505a-505n are configured to provide corresponding non-medical event data 300a-300n to the medical device 510. In this example, the medical device 510 is configured to obtain medical data from a user, to annotate the medical data with one or more of the non-medical event data 300a-300n, and to provide annotated medical data 400 to an analyzer 515.

Although FIG. 5 suggests that the medical device 510 is providing the annotated medical data 400 to a local analyzer 515, in some implementations the analyzer 515 may be a remote device, such as a remote server. For example, in some implementations the medical device 510 may provide the annotated medical data 400 to the server via the Internet. The server, may, for example, be part of a cloud-based platform that includes associated memory devices. The cloud-based platform may, for example, be controlled by a health care provider. Some analytical methods that may be provided by the analyzer 515 are described below.

The medical device 510 may, in some examples, be configured to obtain medical data from one or more other medical devices, which may in some instances be local medical devices. According to some such implementations, the medical device 510 may be configured to annotate the medical data obtained from the one or more other medical devices with one or more of the non-medical event data 300a-300n, and to provide corresponding annotated medical data 400 to the analyzer 515.

Although the flow of information in FIG. 5 is shown as going from the non-medical devices 505a-505n to the medical device 510 and from the medical device 510 to the analyzer 515, some implementations provide various other communications, such as communications between two or more of the non-medical devices 505a-505n, communications between the analyzer 515 and one or more of the non-medical devices 505a-505n, etc. Some implementations provide two-way communications between the non-medical devices 505a-505n and the medical device 510 and/or between the medical device 510 and the analyzer 515.

For example, in some implementations a control system of the medical device 510 may be configured to send a command and/or a query from the medical device 510 to one or more of the non-medical devices 505a-505n. According to some such implementations, the command and/or query may be based on the capabilities of the non-medical device to which the command and/or query is sent. Such capabilities may, in some examples, be determined according to information in the non-medical event data 300, such as the non-medical device model number information that may be provided in field 315, and/or determined according to information that is exchanged during an initial "handshake" between devices. In some examples, a memory system of the medical device 510 (or a memory system that is accessible by the medical device 510) may include a data structure that lists non-medical device model numbers and corresponding non-medical device functionality. According to some examples, the memory system may include a data structure that indicates non-medical device model numbers and corresponding commands and/or queries that the medical device 510 may potentially send to a non-medical device.

For example, if the non-medical device is a coffee maker and the medical device 510 is configured to take blood pressure measurements, a control system of the medical device 510 may be configured to send a command indicating that the coffee maker should stop dispensing coffee for a period of time prior to a blood pressure measurement by the medical device 510. Alternatively, or additionally, a control system of the medical device 510 may be configured to send a query to the coffee machine regarding how much coffee has been dispensed by the coffee machine within a period of time.

In another example, the non-medical device may be a refrigerator and the medical device 510 may be configured to take blood sugar measurements. A control system of the medical device 510 may be configured to send a command indicating that the refrigerator should stop dispensing food for a period of time prior to a blood sugar measurement by the medical device 510. Alternatively, or additionally, a control system of the medical device 510 may be configured to send a query to the refrigerator regarding how much food, what type of food, etc., has been removed from the refrigerator within a period of time.

In some implementations a control system of the analyzer 515 may be configured to send a command and/or a query to the medical device 510 and/or to one or more of the non-medical devices 505a-505n. According to some such implementations, the command and/or query may be based on the capabilities of the medical device or the non-medical device to which the command and/or query is sent. As noted above, such capabilities may, in some examples, be determined according to information in the non-medical event data 300. However, such capabilities also may be determined according to information in the annotated medical data 400, such as the medical device model number information that may be provided in field 415.

In some examples, a memory system of the analyzer 515 (or a memory system that is accessible by the analyzer 515) may include a data structure that lists medical device model numbers and corresponding medical device functionality. The same data structure, or one or more different data structures, may indicate non-medical device model numbers and corresponding non-medical device functionality. According to some examples, the memory system may include a data structure that indicates medical device model numbers and corresponding commands and/or queries that the analyzer 515 may potentially send to the medical device. In some examples the same data structure, or one or more different data structures, may include non-medical device model numbers and corresponding commands and/or queries that the medical device 510 may potentially send to a non-medical device.

In some alternative examples, a non-medical device may be configured to send a command or a query to a medical device. For example, if the non-medical device is a coffee maker and the medical device 510 is configured to take blood pressure measurements, a control system of the non-medical device may be configured to send a command indicating that the medical device 510 should not take a blood pressure measurement for at least an indicated period of time after coffee has been dispensed by the non-medical device.

Figure 6:
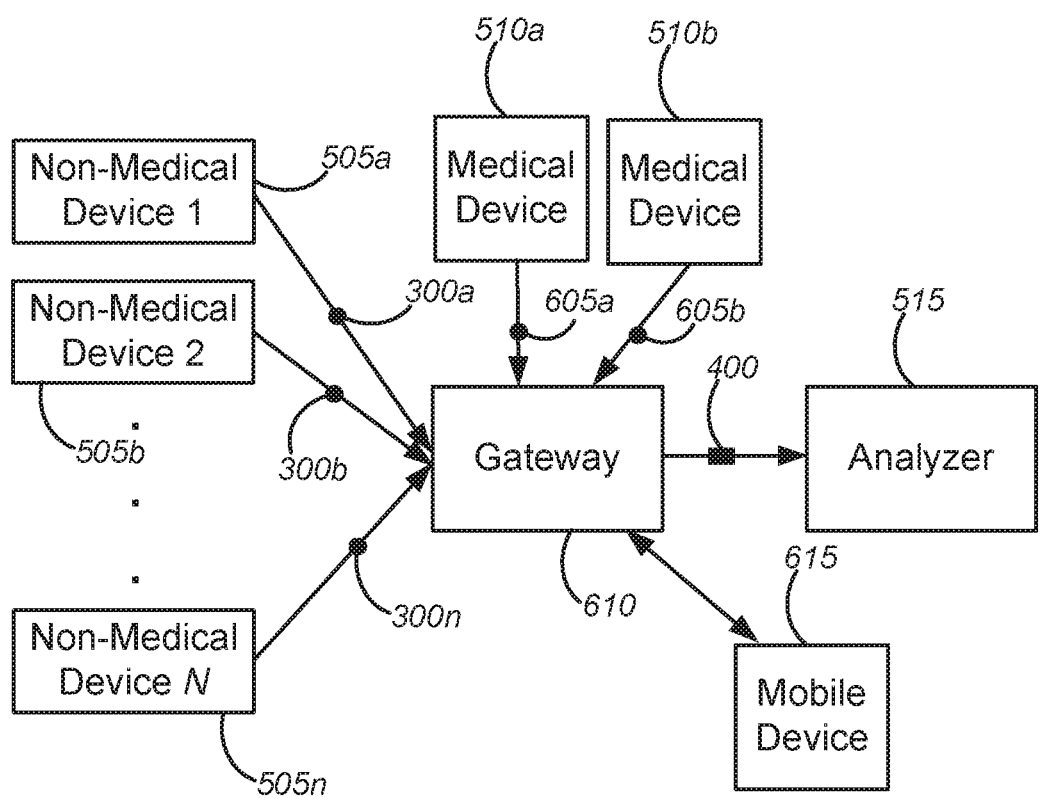
FIG. 6 shows an example of a system in which a gateway device is configured to annotate medical data.

FIG. 6 shows an example of a system in which a gateway device is configured to annotate medical data. The gateway device 610 may include a control system and an interface system, such as the interface system 10 and the control system 15 that are shown in FIG. 1. In this example, non-medical devices 505a-505n are configured to provide corresponding non-medical event data 300a-300n to the gateway device 610. In this example, the gateway device 610 is configured to obtain medical data 605a and 605b from the medical devices 510a and 510b, respectively. Here, the gateway device 610 is configured to annotate the medical data with one or more of the non-medical event data 300a-300n, and to provide annotated medical data 400 to an analyzer 515.

Although FIG. 6 suggests that the gateway device 610 is providing the annotated medical data 400 to a local analyzer 515, in some implementations the analyzer 515 may be a remote device. For example, in some implementations the gateway device 610 may provide the annotated medical data 400 to a server via the Internet.

In some examples, a memory system of gateway device 610 (or a memory system that is accessible by the gateway device 610) may include a data structure that lists medical device model numbers and corresponding medical device functionality. The same data structure, or one or more different data structures, may indicate non-medical device model numbers and corresponding non-medical device functionality. According to some examples, the memory system may include a data structure that indicates medical device model numbers and corresponding commands and/or queries that the gateway device 610 may potentially send to the medical device 510a and/or the medical device 510b. In some examples the same data structure, or one or more different data structures, may include non-medical device model numbers and corresponding commands and/or queries that the gateway device 610 may potentially send to a non-medical device.

Accordingly, some implementations may involve adjusting a time during which medical device data are obtained. Some such implementations may involve adjusting a time during which medical device data are obtained based, at least in part, on received non-medical data. Other implementations may involve adjusting a time during which medical device data are obtained based on a command. The command may, in some instances, be received from a medical device, a non-medical device, a gateway device, an analyzer, or another device (such as the mobile device 615 shown in FIG. 6).

Alternatively, or additionally, some implementations may involve adjusting one or more sensors of a medical device. Some such implementations may involve one or more sensors of a medical device based, at least in part, on received non-medical data. Other implementations may involve adjusting one or more sensors of a medical device based on a command.

Some disclosed implementations involve filtering medical data according to the non-medical event data, to produce filtered medical data. Some such implementations may involve filtering the annotated medical data 400, whereas other implementations may involve filtering un-annotated medical data received from a medical device.

Some such implementations may involve receiving, via an interface system, an indication of one or more limitations on the transmission of filtered medical data and limiting the transmission of filtered medical data according to the indication. Such implementations may enhance a user's privacy by allowing the user to control the medical data that is shared with other people or entities. Alternatively, or additionally, such implementations may allow a user to filter out medical data that is less likely to be accurate or relevant, e.g., by transmitting only data that has at least a threshold reliability indication.

For example, referring to FIG. 6, the gateway 610 is configured for communication with a local device, which is a mobile device 615 in this example. In some implementations, the gateway 610 may receive an indication of one or more limitations on the transmission of filtered medical data from the mobile device 615. The gateway 610 may be configured to limit the transmission of filtered medical data according to the indication.

According to some such implementations, the mobile device 615 may have an interface system and a control system. The interface system may include a user interface system. The user interface system may, for example, include one or more displays with corresponding touch and/or gesture detection systems. In some examples, the user interface system may include one or more microphones and/or speakers. The user interface system may be configured to provide a graphical user interface, or another type of user interface, through which a user may provide input regarding how medical data should be filtered and/or input regarding one or more limitations on the transmission of filtered medical data.

Figure 7:
FIG. 7 shows an example of a graphical user interface that may be used to implement some disclosed methods.

FIG. 7 shows an example of a graphical user interface that may be used to implement some disclosed methods. As with other disclosed implementations, the numbers, types and layout of features in the GUI 700 are merely presented by way of example. Other GUI implementations may include more features, fewer features, different features and/or a different layout of features. In some implementations, the GUI 700 (or a similar GUI) may be used to provide input regarding how medical data should be filtered and/or input regarding one or more limitations on the transmission of filtered medical data.

In alternative implementations, the GUI 700 (or a similar GUI) may be used to obtain user input for analysis of previously-received medical data, non-medical data and/or annotated medical data. In some such implementations, the GUI 700 (or a similar GUI) may be used to obtain user input for the analyzer 515 or for a similar device.

FIGS. 8A-8E show graphs produced by an analyzer according to some examples. In this example, these graphs have been produced according to input received from a user via the GUI 700. The date range indicated in each of FIGS. 8A-8E is the same.

Figure 8A:
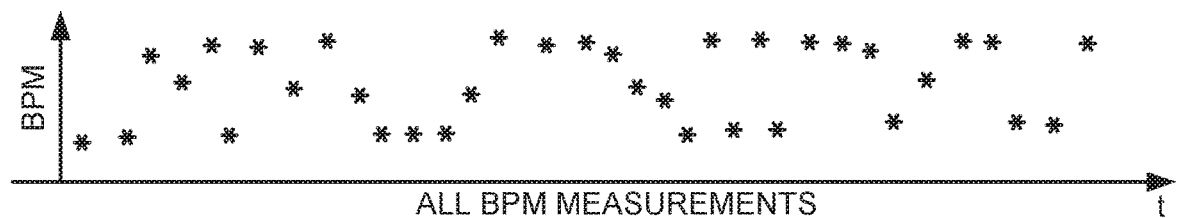
FIGS. 8A-8E show graphs produced by an analyzer according to some examples.

FIG. 8A is a graph that indicates all systolic blood pressure measurements that were taken by a blood pressure monitor within a date range received from a user via the GUI 700. The user may, for example, be the person from whom the blood pressure measurements were obtained, a medical services provider for the person from whom the blood pressure measurements were obtained, etc.

In this example, the person from whom the blood pressure measurements were obtained is named Jack. Jack has been asked by his doctor to measure his blood pressure (BP) 3 times per day. However, as shown in FIG. 8A, these BP measurements alone do not provide a clear indication of Jack's health, because their values fluctuate throughout the day.

In this example, Jack exercises daily. He also makes and drinks between one and three cups of coffee per day. Jack has a coffee machine and an exercise machine that are configured to be IoT nodes. All of the non-medical event data collected by his coffee machine and exercise machine are triggered by Jack, because he lives alone. In this example, these non-medical events (exercise, coffee consumption) are used to annotate Jack's BP measurements. Therefore, the resulting annotated medical data has more meaning and structure than un-annotated BP measurements would have.

Figure 8B:

In order to investigate the possible causes of Jack's BP measurement fluctuation, his doctor has provided a series of inputs to the analyzer 515. FIG. 8B shows a plot of all systolic BP measurements that were taken within the date range, wherein each of the systolic BP measurements was taken within a selected time period after coffee machine activity. The selected time period was 5 minutes in this example. In this example, the average systolic BP reading was 161, which is too high.

Figure 8C:
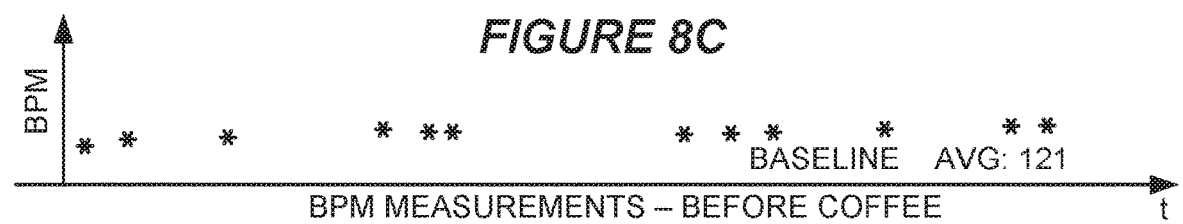
Figure 8D:

FIG. 8C shows a plot of all systolic BP measurements that were taken within the date range, wherein each of the systolic BP measurements was taken prior to a time of coffee machine activity. In this example, the average systolic BP reading was only 121, which is essentially normal. FIG. 8D shows the graphs of FIGS. 8B and 8C and indicates the average change in systolic BP of 40.

Figure 8E:
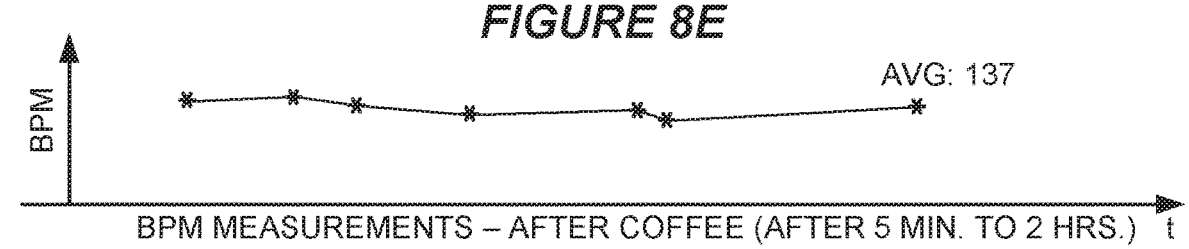

FIG. 8E shows a plot of all systolic BP measurements that were taken within the date range, wherein each of the systolic BP measurements was taken within another selected time period after coffee machine activity. The selected time period was between 5 minutes and 2 hours in this example. In this example, the average systolic BP reading was 137, which is still too high.

After considering the graphs shown in FIGS. 8A-8E, Jack's doctor has a more accurate perception of Jack's health. Jack's heart appears to be essentially healthy, at least with regard to blood pressure. However, it is apparent that Jack drinks too much coffee. The doctor may recommend to Jack that he consume less coffee.

Those of skill in the art will appreciate that the foregoing method descriptions and process flow diagrams are provided merely as illustrative examples and are not intended to require or imply that the steps of the various embodiments must be performed in the order presented. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the claims and the principles and novel features disclosed herein.

The invention claimed is:

1. A medical data annotation apparatus, comprising:
a communication interface system; and
a control system configured to:
  receive, via the communication interface system, medical data from one or more sensors of one or more medical devices;
  receive, via the communication interface system, non-medical event data from one or more non-medical devices, the non-medical event data indicating a non-medical device type and a non-medical event time;
  annotate the medical data according to the non-medical event data to produce annotated medical data, the annotated medical data comprising a data structure comprising a plurality of fields, the plurality of fields comprising the received medical data and the received non-medical event data, the plurality of fields further comprising an identification of the medical device and an identification of the non-medical device; and
  transmit, via the communication interface system, the annotated medical data to another device;
wherein the medical data annotation apparatus is further configured to determine a reliability indication for the medical data based, at least in part, on: (i) a time interval between the non-medical event time and a time at which the medical data was obtained, and (ii) a predetermined threshold for the time interval, and further wherein annotating the medical data involves providing the reliability indication.

2. The apparatus of claim 1, wherein the control system is configured to determine whether to annotate the medical data according to the non-medical event data based, at least in part, on the non-medical event time.

3. The apparatus of claim 1, wherein the annotated medical data includes at least one of non-medical device model number, medical device model number or any combination thereof.

4. The apparatus of claim 1, wherein the apparatus comprises the medical device.

5. The apparatus of claim 4, wherein the control system is configured to send, via the interface system, at least one of a command or a query from the medical device to the non-medical device.

6. The apparatus of claim 1, wherein the apparatus comprises a gateway device.

7. The apparatus of claim 6, wherein the control system is configured to send, via the interface system, at least one of a command or a query to the medical device, to the non-medical device or to both the medical device and the non-medical device.

8. The apparatus of claim 1, wherein the control system is configured to filter the medical data according to the non-medical event data, to produce filtered medical data.

9. The apparatus of claim 8, wherein the control system is configured to:
receive, via the interface system, an indication of one or more limitations on the transmission of filtered medical data; and
limit the transmission of filtered medical data according to the indication.

10. The apparatus of claim 1, wherein the non-medical event data comprises data from a coffee machine, a stove, microwave oven or other food preparation device, an exercise machine, an environmental control device, a lighting device, a toilet, shower or other plumbing device, an entertainment device, a refrigerator, or any combination thereof.

11. The apparatus of claim 1, wherein the one or more medical devices comprise one or more of a blood pressure monitor, a heart rate monitor, a glucometer, a weight scale, a pulse oximeter, an electrocardiogram device, a respiratory rate monitor, a thermometer, a drug delivery device, a bioimpedance monitor, a thermometer, a smart patch, or any combination thereof.

12. The apparatus of claim 1, wherein the control system is configured to adjust one or more sensors of a medical device, to adjust a time during which medical data is obtained, or to adjust both the one or more sensors of a medical device and the time during which medical data is obtained, based at least in part on the non-medical data.

13. A method of annotating medical data using a medical data annotation device comprising a communication interface and a control system, the method comprising:

receiving, by the control system of the medical data annotation device, medical data from one or more sensors of one or more medical devices;

receiving, by the control system, non-medical event data from one or more non-medical devices, the non-medical event data indicating a non-medical device type and a non-medical event time;

annotating, via the control system, the medical data according to the non-medical event data, to produce annotated medical data, the annotated medical data comprising a data structure comprising a plurality of fields, the plurality of fields comprising the received medical data and the received non-medical data, the plurality of fields further comprising an identification of the medical device and an identification of the non-medical device; and transmitting, via the communication interface system of the medical data annotation device, the annotated medical data to a second device;

wherein the medical data annotation device is further configured to determine a reliability indication for the medical data based, at least in part, on: (i) a time interval between the non-medical event time and a time at which the medical data was obtained, and (ii) a predetermined threshold for the time interval, and further wherein annotating the medical data involves providing the reliability indication.

14. The method of claim 13, further comprising determining, via the control system, whether to annotate the medical data according to the non-medical event data based, at least in part, on the non-medical event time.

15. The method of claim 13, wherein the first device comprises the medical device, further comprising sending at least one of a command or a query from the medical device to the non-medical device.

16. The method of claim 13, wherein the first device comprises a gateway device, further comprising sending at least one of a command or a query to the medical device, to the non-medical device or to both the medical device and the non-medical device.

17. The method of claim 13, further comprising filtering, via the control system, the medical data according to the non-medical event data, to produce filtered medical data.

18. The method of claim 17, further comprising:
receiving, by the control system, an indication of one or more limitations on the transmission of filtered medical data; and
limiting, by the control system, the transmission of filtered medical data according to the indication.

19. The method of claim 13, further comprising adjusting, by the control system, one or more sensors of a medical device, a time during which medical data is obtained, or both the one or more sensors of a medical device and the time during which medical data is obtained, based at least in part on the non-medical data.

20. A medical monitoring device configured to improve health monitoring of an individual by providing annotated medical data comprising:
a medical sensor configured to obtain medical data from the individual;
a communication interface configured to obtain non-medical sensor data about the individual, the non-medical device comprising a non-medical sensor configured to obtain the non-medical data; and
a processor configured to:
receive the medical data from the medical sensor;
receive non-medical data, the non-medical event data indicating a non-medical device type and a non-medical event time; and
annotate the medical data according to the non-medical data to produce annotated medical data, the annotated medical data comprising a data structure comprising a plurality of fields, the plurality of fields comprising the received medical data and the received non-medical data, the plurality of fields further comprising an identification of the medical device and an identification of the non- medical device type;
wherein the communication interface is further configured to transmit the annotated medical data to a second device;
wherein the medical monitoring device is further configured to determine a reliability indication for the medical data based, at least in part, on: (i) a time interval between the non-medical event time and a time at which the medical data was obtained, and (ii) a predetermined threshold for the time interval, and further wherein annotating the medical data involves providing the reliability indication.

21. The medical monitoring device of claim 20, wherein the processor is further configured to determine whether to annotate the medical data according to the non-medical data based, at least in part, on the non-medical event time.

22. The medical monitoring device of claim 20, wherein the processor is further configured to send at least one of a command or a query from the medical monitoring device to the non-medical device.

23. The medical monitoring device of claim 20, wherein the processor is further configured to filter the medical data according to the non-medical event data, to produce filtered medical data.

24. A medical monitoring system configured to obtain, annotate, and transmit medical and non-medical information about an individual, comprising:
a medical device comprising: (i) a medical sensor configured to obtain medical data from the individual, (ii) a communication interface system; and (iii) a processor;
a non-medical device comprising a non-medical sensor configured to obtain non- medical data about the individual;
wherein the processor of the medical device is configured to:
receive the medical data from the sensors;
receive, via the communication interface system, the non-medical data from the non-medical device, the non-medical data indicating a non-medical device type and a non-medical event time;
annotate the medical data according to the non-medical event data to produce annotated medical data, the annotated medical data comprising a data structure comprising a plurality of fields, the plurality of fields comprising the received medical data and the received non-medical data, the plurality of fields further comprising an identification of the medical device and an identification of the non-medical device type; and
transmitting, via the communication interface system, the annotated medical data to another device;
wherein the medical monitoring system is further configured to determine a reliability indication for the medical data based, at least in part, on: (i) a time interval between the non-medical event time and a time at which the medical data was obtained, and (ii) a predetermined threshold for the time interval, and further wherein annotating the medical data involves providing the reliability indication.

25. The medical monitoring system of claim 24, wherein the processor is further configured to determine whether to annotate the medical data according to the non-medical data based, at least in part, on the non-medical event time.

\* \* \* \* \*